United States Patent
Zeuch et al.

(10) Patent No.: US 9,670,448 B2
(45) Date of Patent: Jun. 6, 2017

(54) BIOREACTOR, REACTOR BAG FOR SAME AND STIRRER FOR CIRCULATING CONTENTS OF SAID BAG

(71) Applicant: Sartorius Stedim Biotech GmbH, Goettingen (DE)

(72) Inventors: Stefan Zeuch, Goettingen (DE); Thomas Regen, Goettingen (DE); Gerhard Greller, Goettingen (DE); Oscar-Werner Reif, Hannover (DE)

(73) Assignee: Sartorius Stedim Biotech GmbH (DE)

( * ) Notice: Subject to any disclaimer, the term of this patent is extended or adjusted under 35 U.S.C. 154(b) by 189 days.

(21) Appl. No.: 14/435,275

(22) PCT Filed: Aug. 2, 2013

(86) PCT No.: PCT/EP2013/066301
§ 371 (c)(1),
(2) Date: Apr. 13, 2015

(87) PCT Pub. No.: WO2014/060130
PCT Pub. Date: Apr. 24, 2014

(65) Prior Publication Data
US 2015/0259638 A1    Sep. 17, 2015

(30) Foreign Application Priority Data
Oct. 18, 2012    (DE) .................. 10 2012 020 384

(51) Int. Cl.
*C12M 1/06*    (2006.01)
*C12M 1/02*    (2006.01)
(Continued)

(52) U.S. Cl.
CPC .......... *C12M 27/02* (2013.01); *B01F 13/0827* (2013.01); *B01F 15/0085* (2013.01); *C12M 23/14* (2013.01); *C12M 23/28* (2013.01)

(58) Field of Classification Search
CPC ...... C12M 27/02; C12M 23/14; C12M 23/28; B01F 13/0827; B01F 15/0085
(Continued)

(56) References Cited

U.S. PATENT DOCUMENTS 8,123,199 B2    2/2012    Terentiev et al.
2010/0197003 A1    8/2010    Terentiev et al.
(Continued)

FOREIGN PATENT DOCUMENTS

DE    20 2007 005 868    8/2007
DE    20 2009 006 840    8/2009
(Continued)

OTHER PUBLICATIONS

International Appl. No. PCT/EP2013/066301—International Preliminary Report on Patentablity, English Translation Apr. 21, 2015.
(Continued)

*Primary Examiner* — Michael Hobbs
(74) *Attorney, Agent, or Firm* — Gerald E. Hespos; Michael J. Porco; Matthew T. Hespos (57) ABSTRACT

A bioreactor has a reactor bag (12) with a predominantly flexible bag wall (121) that has a rigid bearing area. A stirrer arrangement (14) is in the bearing area and includes rigid profile ring (16) made of a non-magnetic material and fixed in the bearing area. The stirrer arrangement (14) also includes a shaftless stirrer (18) rotatably engaged with the profile ring (16) and having parts that are permanently magnetic. An electric coil arrangement (20) is outside the reactor bag (12) and can produce a rotating magnetic field that interacts with the permanent-magnetic areas of the stirrer (18) to produce a torque that rotates the stirrer (18) and circulates the contents of the bag (12).

15 Claims, 5 Drawing Sheets

(51) Int. Cl.
  *C12M 1/00* (2006.01)
  *B01F 13/08* (2006.01)
  *B01F 15/00* (2006.01)
(58) Field of Classification Search
  USPC .................................................... 435/289.1
  See application file for complete search history.

(56) References Cited

U.S. PATENT DOCUMENTS

2011/0013473 A1  1/2011  Ludwig et al.
2011/0058447 A1  3/2011  Reif et al.

FOREIGN PATENT DOCUMENTS

| EP | 2 065 085 | 6/2009 |
| WO | 03/028869 | 4/2003 |
| WO | 2008/040567 | 4/2008 |
| WO | 2009/116002 | 9/2009 |
| WO | 2009/122310 | 10/2009 |
| WO | 2013/040161 | 3/2013 |

OTHER PUBLICATIONS

International Search Report of Oct. 24, 2013.
German Office Action of Oct. 10, 2013.

BIOREACTOR, REACTOR BAG FOR SAME AND STIRRER FOR CIRCULATING CONTENTS OF SAID BAG

BACKGROUND

1. Field of the Invention

The invention relates to a bioreactor, comprising
- a reactor bag with a predominantly flexible bag wall which has a rigidly formed bearing area for housing a stirrer serving to circulate contents of the bag,
- a shaftless stirrer, parts of which are permanently magnetic, housed inside the bag in the bearing area, and
- a coil arrangement positioned outside the reactor bag with which coil arrangement a rotating magnetic field can be produced, which magnetic field interacts, in a manner exerting a torque on the stirrer, with the permanent-magnetic areas thereof.

2. Description of the Related Art

The invention further relates to a reactor bag for a bioreactor, comprising a predominantly flexible bag wall which has a rigidly formed bearing area for housing a shaftless stirrer serving to circulate the contents of the bag, at least parts of the stirrer being permanently magnetic.

Finally, the invention relates to a stirrer to circulate the contents of a bioreactor, parts of which stirrer being permanently magnetic and comprising a plurality of paddle-like circulation elements affixed to a holder.

Such bioreactors, reactor bags and stirrers for same are known from U.S. Pat. No. 8,123,199 B2.

As is known, bioreactors serve as containers for fluids in which biological processes, such as fermentation or cell growth, are intended to take place in a controlled manner. Due to the metabolic activity of the microorganisms involved, local changes arise in the concentration of various chemical components. To maintain the same, or at least controlled, concentration conditions in the entire container, the fluid in the reactor must be stirred occasionally; preferably, in a constant manner. To avoid contamination, the stirrers are generally arranged in the interior of the otherwise closed reactor container (except for specific inlets and outlets). One difficulty is causing the stirrers located in the interior of the reactor container to move in the desired stirring direction by means of drive mechanisms usually arranged outside of the reactor container.

For bioreactors with rigid walls, such as steel tanks, a familiar solution is to affix the actual circulation elements of the stirrer, such as impellers, on a shaft that penetrates the container wall in a sealed bearing such that the stirrer shaft can simply be coupled with the drive shaft of a motor of any desired configuration.

Recently there has been a steady increase in the use of bioreactors whose actual container is designed as a flexible bag for single use. Advantages include the cost-effective manufacture of the foil bags, straightforward and space-saving storage, ease of sterilization and contamination security, as well as dispensing with the need for laborious cleaning after use. However, the problem of appropriately circulating the contents of the bag has not been definitively solved. In particular, versions with stirrer shafts that penetrate the bag wall are regarded as disadvantageous as this increases the risk of contamination, considerably increases the amount of space required for storage and, because of the necessity of providing a sealed penetration point for the shaft, renders the manufacture of the bags more complicated and expensive.

The category-defining patent U.S. Pat. No. 8,123,199 B2 discloses a shaftless stirrer having a plurality of impellers around a flat, cylindrical holder, wherein the flat, cylindrical holder is housed in a correspondingly shaped rigid vessel forming the bottom of the reactor bag. At least part of the cylindrical holder is designed to be permanently magnetic and interacts with an external magnetic field that penetrates the vessel wall. The external magnetic field is designed as a rotational field, so that the stirrer holder, along with the paddle-like circulation elements, is caused to rotate in its bearing vessel. This known device has several disadvantages. On the one hand, it is limited in that the position of the stirrer is restricted to the bottom region of the reactor bag, which can be expected to result in insufficient mixing of the reactor contents in tall bioreactors. On the other hand, the stirrer is not axially fixed in its bearing vessel—rather, to the contrary, in order to reduce bearing friction, axial raising of the stirrer by the external magnetic field is described. This means that during transport, the stirrer can easily fall out of its bearing and damage the bag walls with its sharp-edged paddles.

It is the problem of the present invention to further develop category-defining bioreactors, reactor bags and stirrers so as to overcome the disadvantages of the prior art. In particular, bioreactors and/or reactor bags with significantly reduced space requirements during storage and/or transport are to be provided. Also improved mixing of the reactor contents and safer transport and storage options are intended to result.

SUMMARY OF THE INVENTION

This problem is solved in that a rigid profile ring made of non-magnetic material, e.g. plastic, is arranged in a segment of height of the reactor bag—however preferably not at the height of its top edge—as a bearing area in which the stirrer formed as the rotor spanning the cross-section of the bag is rotatably housed by means of a guide rail, the magnetic field of the electric coil arrangement interacting with at least one permanent magnet arranged in the radially outer area of the rotor.

The problem is further solved in that a rigid profile ring made of a non-magnetic material, e.g. plastic, is arranged as a bearing area at a segment of height of the reactor bag—however preferably not at the height of its top edge—in which the stirrer formed as the rotor spanning the cross-section of the bag is rotatably housed in an axial and radial manner by means of a guide rail.

The problem also is solved in that the stirrer is formed as a rotor having a central body and at least three spokes extending radially from the central body, the rotor having at least one permanent magnet arranged in its radially outer area and at least one guide element of an outer guide rail.

The essential subject of the invention is the special design of the bearing area and the corresponding design of the stirrer. The stirrer spans the entire cross-section of the bag and is housed in a profile ring which forms the rails of a guide rail at its radially outer area, the profile ring extending around the circumference of the reactor bag. The magnetic interaction to drive the stirrer in a motorized way also takes place in this radially outer mechanical interaction area between the rotor and its guide. The magnetic forces acting between the outer coil arrangement and the permanent magnet(s) arranged in the outer area of the stirrer penetrate the profile ring, which therefore must be made of a non-magnetic material, e.g. plastic. The entire stirrer arrangement can therefore be designed such that it occupies only very minimal axial space in the apparatus and moreover can be arranged at any desired axial position within the reactor bag. It is also conceivable that multiple such stirrer arrangements could be arranged at different axial positions within the reactor bag so as to ensure sufficient mixing of the entire reactor content in very tall bioreactors. Due to the minimal axial height of each stirrer arrangement, the walls of the reactor bag, which are inherently flexible, are only reinforced with "ribs", flexible wall areas remaining between these profile rings forming the "ribs" such that the reactor bag can be compressed like a bellows for storage and transport, which significantly reduces the storage space required. With appropriate design of the guide rail, it will be impossible for any of the rotors to dislodge from their guides, which means that there is no risk of the bag walls being damaged in the compressed state and that in the expanded state, it is possible to begin stirring operation immediately without any prior assembly steps.

In a preferred embodiment, the profile ring penetrates the flexible bag wall and is bonded to it. The bonded connection, which can be implemented by means of welding or gluing, ensures the seal-tightness of the reactor bag, including in the area of the stirrer arrangement. Since the profile ring radially penetrates the bag wall, direct access to its external side is ensured from outside of the reactor bag. This feature takes on special importance in connection with the special designs of the motorized stirrer drive described below. However, it is generally also conceivable that the profile ring be bonded to the internal side of the otherwise flexible bag wall, the bag wall covering the radially external contours of the profile ring tightly. This version is generally reserved for devices with very thin, preferably elastic, bag wall material.

The profile ring preferably has a circumferential guide groove open to the bag interior in which at least one guide shoe arranged radially outside of the rotor is guided axially and radially. Special design versions of the guide shoe for rotors of different designs are discussed below. However, with respect to all such embodiments, the guide shoe is surrounded by the guide groove on at least three sides, such that both radial and axial support is ensured in this type of bearing.

Alternatively, it is also conceivable that the profile ring have a circumferential ridge oriented to the bag interior, which ridge projects into at least one groove element arranged at the radially outer side of the rotor such that the rotor is guided axially and radially. This version essentially represents the kinematic reverse of the preferred embodiment described above. One skilled in the art will easily be able to translate the embodiments of the groove-guided guide shoe described in detail below to the corresponding kinematically reversed embodiments with a ridge-guided groove element.

To reduce friction, a further development of the invention provides that at no fewer than three positions on the circumference of the profile ring, radially oriented roller bearings and/or axially oriented, opposing pairs of roller bearings project into the guide groove with spring action, or, in embodiments with a guide ridge, project out of it.

Alternatively or additionally to this, it is conceivable that at no fewer than three positions on the circumference of the profile ring, radially oriented slide bearing springs and/or axially oriented, opposing pairs of slide bearing springs project into the guide groove, or, in embodiments with a guide plane, project out of it. The surfaces of the slide bearing springs are preferably coated with friction-reducing material, such as polytetrafluoroethylene.

Of course, in principle, it is also conceivable that such or similar friction-reducing elements be provided on the rotor, especially on the guide shoe and/or on the groove element. The reason for the general preference for embodiments with a guide groove as opposed to embodiments with a guide ridge is the special suitability of the former for an especially advantageous further development of the invention. This provides that the guide groove on the exterior side of the profile ring form a projection having at least one axial mounting surface on which an electric coil arrangement designed as a separate unit or unit group is arranged and/or arrangeable, the coil arrangement being capable of generating the magnetic field. In this connection, an axial mounting surface is to be understood as a surface with surface normals oriented parallel to the axial direction on which a mounting element, in this case the electric coil arrangement in particular, is arrangeable such that a radial overlap occurs. In this way, a radial overlap of the guide shoe guided in the interior of the guide groove with the coil arrangement arranged on the exterior axial mounting surface can be realized, which serves to minimize the distance between the coil arrangement that generates the magnetic field and a permanent magnet arranged in the external region of the stirrer, or potentially even in the area of the guide shoe. This serves to maximize the interaction between the permanent magnet and the coil arrangement such that only small permanent magnets and/or low coil currents are required to achieve a predetermined drive power. It is advantageous if there is more than one axial mounting surface.

Rather, it is preferred that the guide groove on the exterior side of the profile ring be surrounded on three sides, by a form-fitting connection, by an electric coil arrangement designed as a separate unit or unit group, which coil arrangement is capable of generating the magnetic field. The interaction between the coils and permanent magnets can be yet further augmented by means of this measure.

One skilled in the art recognizes that the rearward accessibility of the profile ring has special importance in connection with this embodiment. In particular, this makes it conveniently possible to separate elements intended for single use (bag, rotor and profile ring) from reusable elements (coil inserts).

Regarding the design of the rotor, it is preferable that it have a central body and at least three spokes radially extending from the central body. This can be realized for example as a propeller-like rotor design in which the spokes are designed as paddles arranged in a hydrodynamically advantageous manner in order to effect the desired mixing of the reactor contents and to minimize shear forces affecting the cells in cell cultures within the bioreactor.

In another preferred embodiment, the spokes of the rotor are connected to one another by means of a ring-shaped rim. In this embodiment, the rotor has the form of a spoked wheel in which the actual circulation elements, i.e. the impellers, can also be realized by designing the spokes in a special way.

In both embodiments mentioned, i.e. the rotor designed in the form of a propeller and spoked-wheel, respectively, the circulation elements can also be arranged in the area of the central body. In this case, it would be necessary to design the spokes, to the extent possible, so that they would exert the lowest possible hydrodynamic resistance to the rotation of the rotor.

While with respect to the design of the rotor as a propeller the permanent magnets that interact with the coil arrangement are arranged together with the guide elements designed as sliding blocks or groove elements in the area of the propeller blade tips, it is preferred, in the case of the rotor being designed as a spoked-wheel, that a plurality of permanent magnets be arranged around the circumference of the rim. Depending on the embodiment, the rim itself can serve as a ring-shaped guide shoe. Alternatively, multiple isolated areas of the rim can be designed as sliding block-like guide shoes while the areas of the rim in between serve only to hold magnets. It is also conceivable that the spokes penetrate the rim radially such that a structure similar to a ship's helm results, where the magnets are located on the rim ring, and the sliding block-like guide shoes or groove elements are located in the area of the spoke tips. The inverse arrangement is also conceivable, in which the magnets are located in the area of the spoke tips while the sections of the rim in between serve as guide elements. This version renders radial guiding more difficult, however.

One skilled in the art will recognize that the motorized drive is preferably implemented in the form of a linear motor with a circular, curved long stator in which the sections of the rotor that bear the magnets or magnet groups can be regarded as sliders connected to one another. By controlling the coil arrangements to produce a rotating magnetic field, such as in the form of a three-phase alternating current, the armatures will move synchronously toward one another along the circular path provided by the guide rail of the profile ring. The mechanical connection of the sliders in the propeller- or spoked wheel-shaped rotor results in rotational motion of the rotor. Of course, it is also possible to create such rotational motion if only a single slider is provided, i.e. only one single rotor area bearing one or more magnets.

Further features and advantages of the invention result from the following specific description and the drawings.

DETAILED DESCRIPTION OF PREFERRED EMBODIMENTS

Figure 14:
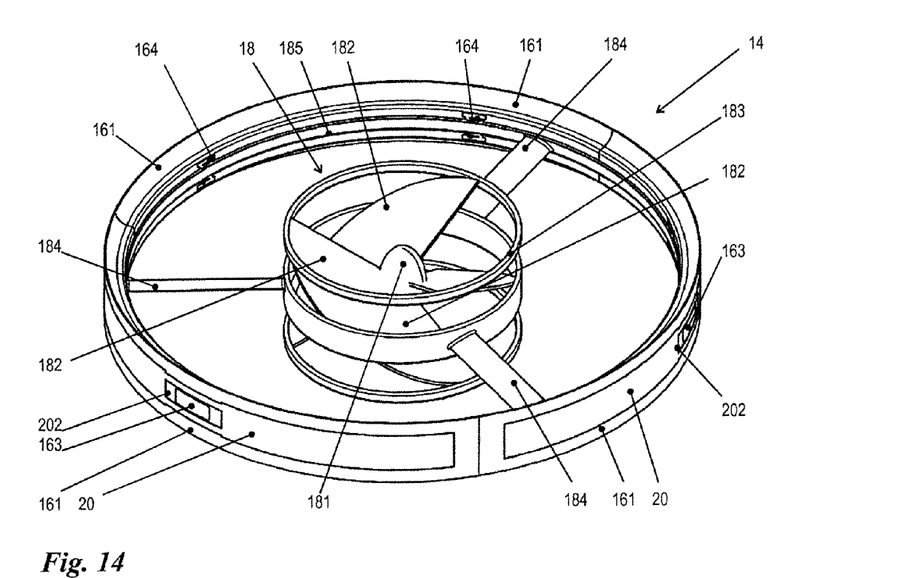
FIG. 14 a perspective view of a stirrer arrangement composed of a stirrer, profile ring and coil inserts.
Figure 15:
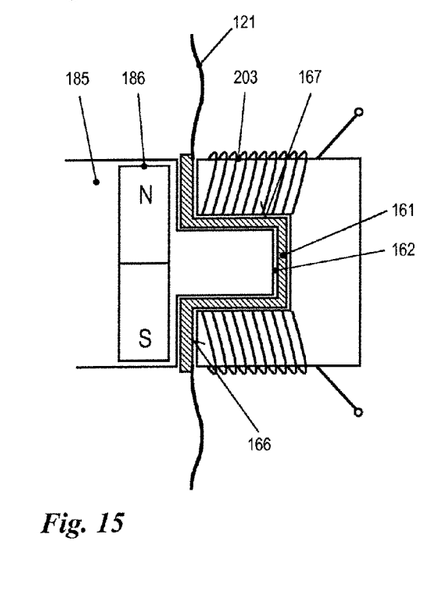
FIG. 15 a schematic view of a possible coil/magnet configuration.

FIGS. 1 to 14 illustrate as an example a preferred embodiment of the invention and will be discussed together, unless specific reference is made to a particular figure. FIG. 15 and show, purely schematically and as an example, two possible coil/magnet configurations to implement the motorized drive of a stirrer arrangement in accordance with the invention, especially a stirrer arrangement in accordance with FIGS. 1 to 14. Identical reference numbers in the figures indicate identical or analogous elements.

Figures 1, 2:
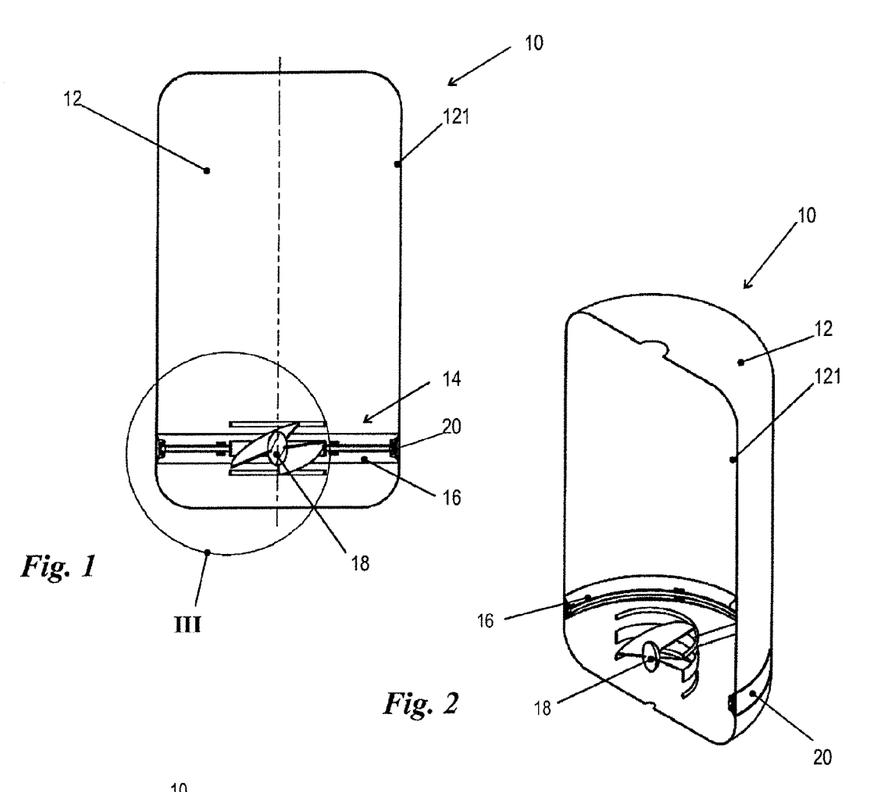
FIG. 1 a schematic cross-sectional view of a bioreactor in accordance with the invention.
FIG. 2 a perspective sectional view of the bioreactor in accordance with the invention.
Figure 3:
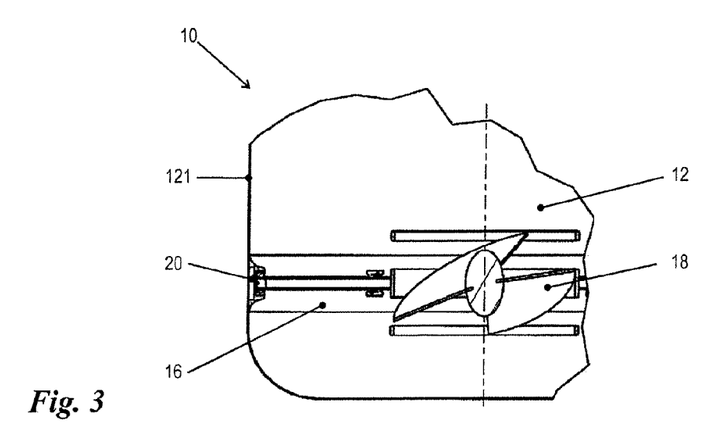
FIG. 3 an enlarged view of a section of FIG. 1.

FIGS. 1 to 3 show highly schematic views of a bioreactor that has a reactor bag 12 and a stirrer arrangement 14. The reactor bag 12 has a predominantly flexible bag wall 121 that is made rigid only in the area of the stirrer arrangement 14 by the latter's profile ring 16, which is made of a rigid, non-magnetic material, e.g. plastic. Preferably, the bag wall 121 is interrupted in the area of the stirrer arrangement 14 and is at least partially replaced by the profile ring 16. The axial edge areas of the latter can be affixed to the bag wall by gluing or welding, for example. It is irrelevant whether the profile ring 16 is bonded to the interior or to the exterior side of the bag wall 121. Ultimately, the bag wall 121 and the profile ring 16 together form a sealed container that is made rigid in rib-like fashion only in the area of the profile ring and is otherwise flexible. The exterior side of the profile ring 16 is accessible from the exterior of the bag.

FIGS. 1 to 3 do not show inlets and outlets usually provided on bioreactors; however, one skilled in the art would be able to include them depending on the requirements of a specific individual case. Also not shown is a bag holder serving as a bracket or support structure for hanging or supporting, respectively, the reactor bag 12, which bag holder can be designed as a bracket frame to place the reactor bag 12 on or as an exoskeleton-like container to accommodate the reactor bag 12. In the latter case in particular, it is possible to arrange the coil inserts, described in more detail below, in the wall of the exoskeleton container such that they are automatically introduced into the profile ring in their deployment position when the reactor bag 12 is inserted or when the exoskeleton container is closed, respectively.

In addition to the profile ring 16, the stirrer arrangement comprises a rotor 18 rotatably housed in an axial and radial manner in the profile ring, as well as the coil inserts 20 which, although previously mentioned, are hardly visible in FIGS. 1 to 3. A stirrer arrangement 14 isolated from the reactor bag 12 is shown in FIG. 14. Its individual elements are described in more detail below in connection with the remaining figures.

One skilled in the art will easily recognize that the bioreactor 10 in accordance with the invention is not limited to versions with only one stirrer arrangement 14. Rather, it is possible, especially for very tall bioreactors, to position multiple stirrer arrangements 14 at various axial heights. The flexibility of the bag wall 121 in the area between the stirrer arrangements 14 results in a bellows-like or accordion-like compressibility, which causes the storage space to be very small, even with multiple stirrer arrangements 14.

Figure 4:
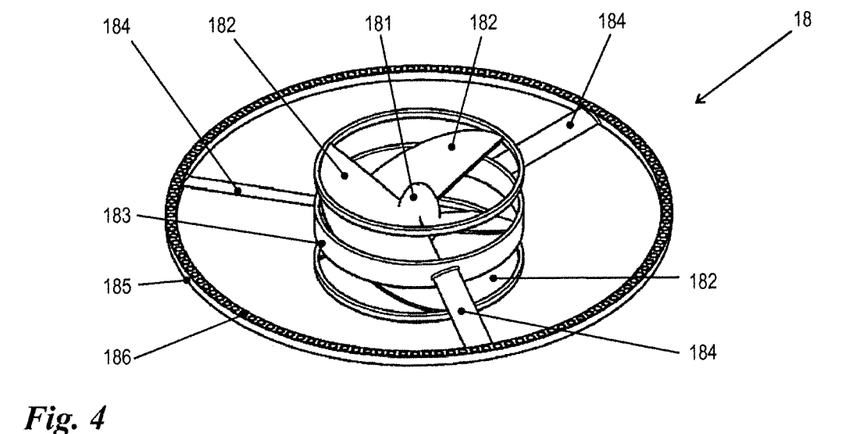
FIG. 4 a perspective view of a stirrer in accordance with the invention.
Figure 5:
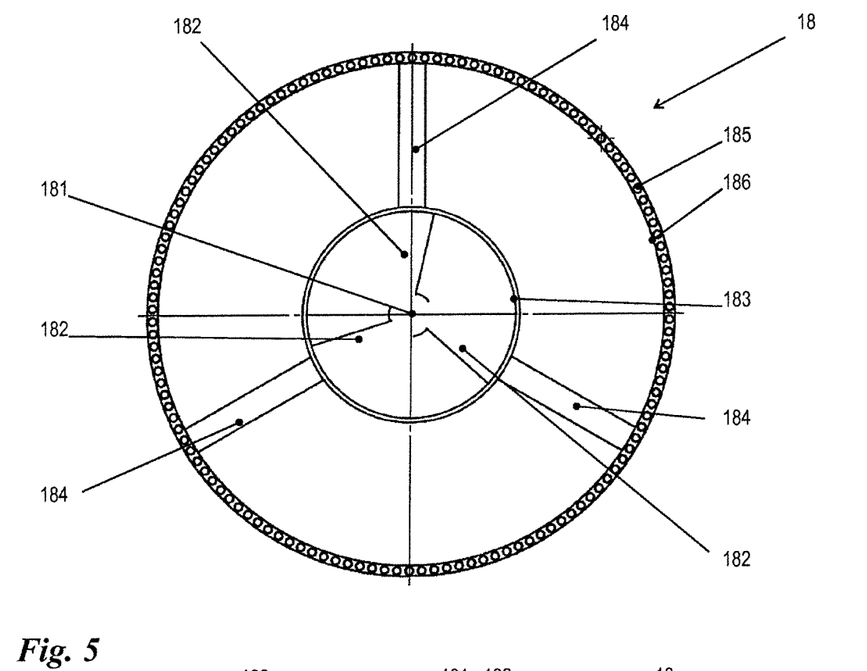
FIG. 5 a top view of the stirrer in FIG. 4.
Figure 6:
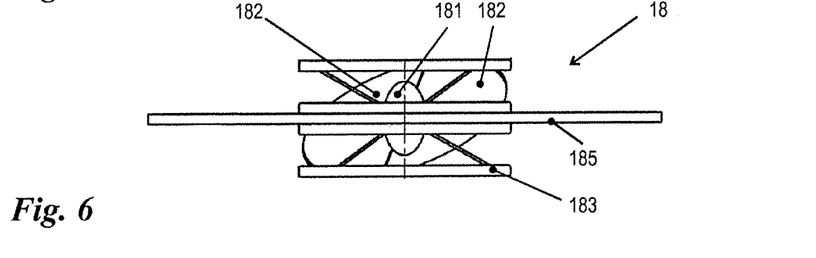
FIG. 6 a lateral view of the stirrer in FIG. 4.

FIGS. 4 to 6 show various views of a preferred embodiment of a rotor 18. The actual stirring function is carried out by the elements in the central area of the rotor 18. In the embodiment shown, these elements are a central body 181, which is preferably designed in a flow-optimized form, as shown, which provides especially low hydrodynamic resistance to an axial flow. Propeller-like paddles 182, which are to be regarded as the actual circulation elements, are molded to the central body 181. The impellers 182 can be given a special design in accordance with standard hydrodynamic criteria, taking into account the requirements of the individual case, especially taking into account the viscosity of the fluid to be stirred as well as the desired rotations per minute. In the embodiment shown, the stirring structure consisting of the central body 181 and the impellers 182 is arranged in a cage 183 that serves, on the one hand, to stabilize the stirring structure and on the other, to effect the mechanical connection between it and the motorized drive described further below. For this purpose, multiple spokes 184 extending radially are molded onto the cage 183. These spokes 184 preferably have a flow-optimized profile. What specifically is regarded as favourable depends on the requirements of the individual case. A profile form that offers as little resistance as possible can be chosen; on the other hand, it is also possible to design the spokes 184 similarly to the impellers 182 as effective circulation elements. The spokes 184 connect the cage 183 with a rim ring 185, which, as described in more detail below, is rotatably housed in the profile ring 16. The rim ring 185 therefore serves as the guide shoe that runs around the entire circumference. In the embodiment shown, the rim ring 185 also serves to bear a plurality of permanent magnets 186 which are inset within it. Preferably this is done such that the magnets 186 do not project axially above the rim ring. It is preferable for them to be molded inside the plastic material of which the rim ring 185 is made.

In an alternative embodiment that is not shown, a continuous rim ring 185 can be dispensed with. In this embodiment, only the radially outer tips of the spokes 184 are formed as isolated guide shoes; one or more of which can bear the magnets 186.

FIGS. 7 to 10 show a segment 161 of the profile ring 16 in an especially preferred embodiment. Although in principle it is possible to design the basic structure of the profile ring 16 as a single piece, it has been shown to be advantageous, with regard to the assembly of a reactor bag in accordance with the invention and/or a bioreactor in accordance with the invention, to design the profile ring 16 in the form of multiple, preferably identical profile ring segments 161.

The basic structure of the profile ring segment 161 consists of a curved plastic profile strip, the inner side of which has a guide groove 162. The width of this groove correspond to the rim ring 185 of the rotor 18 such that the latter is housed axially and radially with little play in the guide groove 162. Preferably, the appropriate amount of play is adapted to the intended contents of the reactor. In cell cultures in particular, provision of too little play can result in undesired crushing of cells that get between the rim ring 185 and guide groove 162. It is therefore preferable that the amount of play be greater than the minimum required to maintain the rotational capacity of the rotor 18 and that groove formation on the rotor 18 be prevented by special rolling bearing elements or slide bearing elements 163, 164. Multiple radial bearings 163 and axial bearings 164 are therefore distributed around the circumference of the profile ring in the embodiment shown. In the preferred embodiment, the radial bearings 163 each consist of two rollers housed in radial spring bearings, whose axis of rotation is oriented parallel to the axis of rotation of the rotor 18. These pairs of rollers housed in spring bearings project radially from the exterior into the guide groove 162. If at least (preferably exactly) three such radial bearings 163 are provided, the rim ring 185 of the rotor 18 is held elastically in a centered position. The axial bearings 164 are designed as spring-pretensioned roller pairs arranged axially opposite on either side of the guide groove 162, with radially oriented axes of rotation that center the rim ring 185 of the rotor 18 axially and elastically in the guide groove 162.

Figure 7:
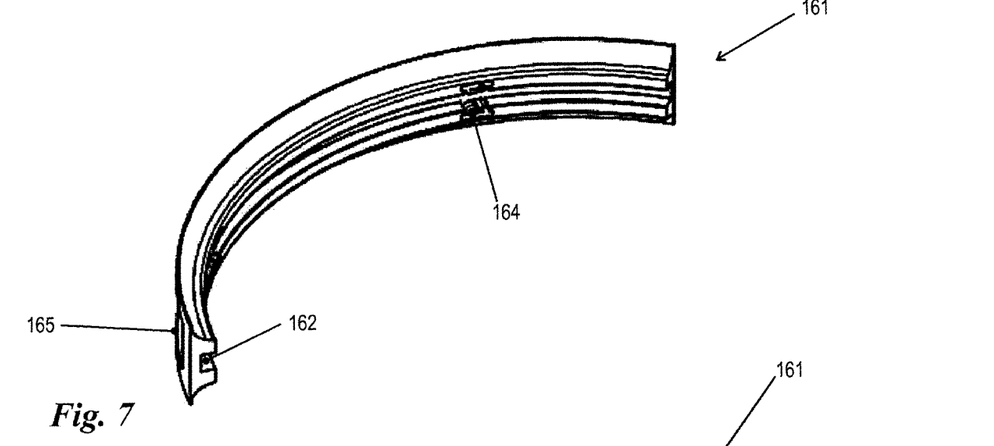
FIG. 7 a perspective view of a segment of a profile ring for housing the stirrer.
Figure 8:
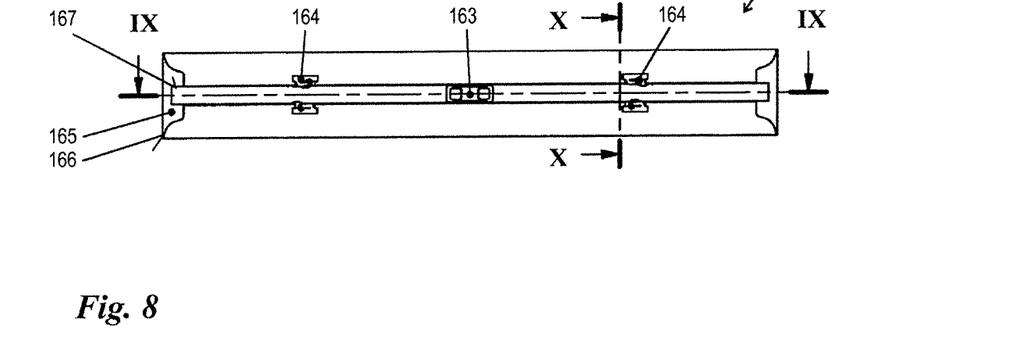
FIG. 8 a lateral view of the interior side of the profile ring segment in FIG. 7.
Figures 9, 10:
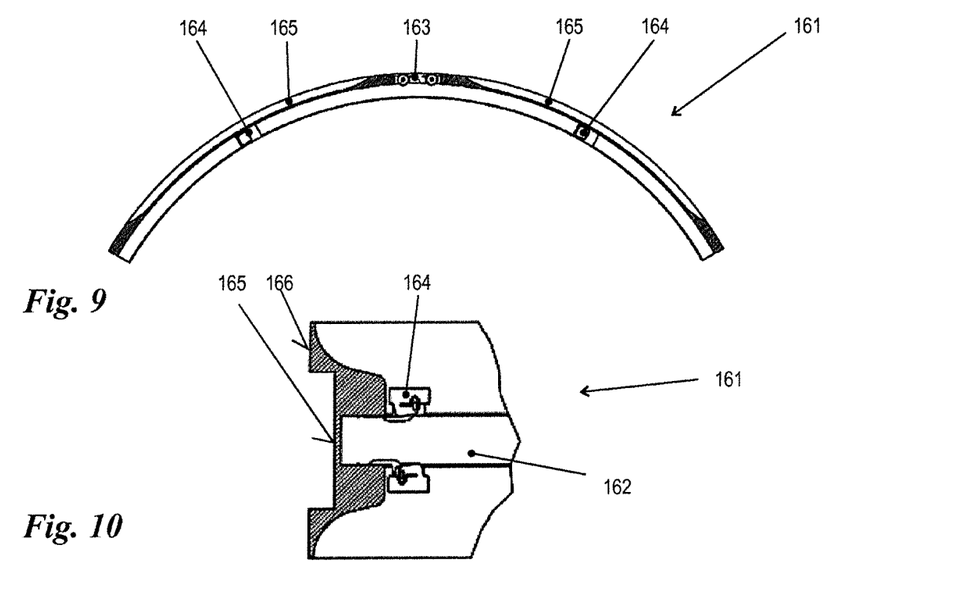
FIG. 9 a sectional view of the profile ring segment from FIG. 7 along the cutting plane x-x in FIG. 8.
FIG. 10 a sectional view of the profile ring segment from FIG. 7 along the cutting plane IX-IX in FIG. 8.

It is clearly apparent in FIGS. 7 and 10 in particular that the profile ring segment 161 has a recess 165 on its outer side. This is flanked axially on both sides by the radial mounting surfaces 166 that serve to fasten the flexible bag wall 121 to the profile ring 16. In particular, they can serve as contact surfaces for a bonded connection, especially by gluing or welding. In the area of a bearing 163, 164, the recess 165, as is especially evident in FIGS. 9 and 10, is less deep or is interrupted, respectively. However, the recess 165 is deep enough between the bearings that a radial overlap of the recess 165 and the guide groove 162 results. In other words, the radially outer wall of the guide groove 162 forms an axial mounting surface 167 on which the electric coils can be mounted and positioned there at a minimal distance to the permanent magnets 186 within the rim ring 185 that runs within the guide groove 162.

Figure 11:
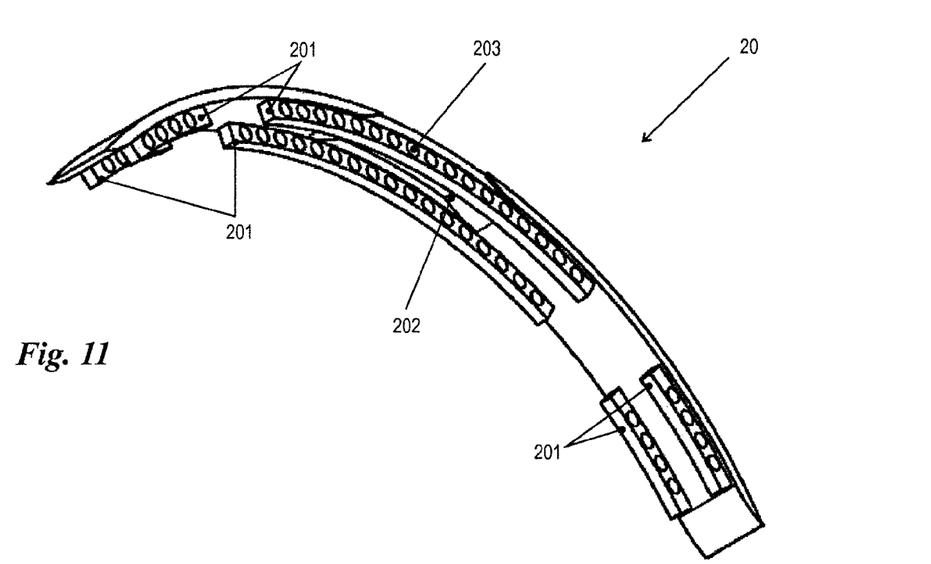
FIG. 11 a perspective view of a coil insert.
Figure 12:
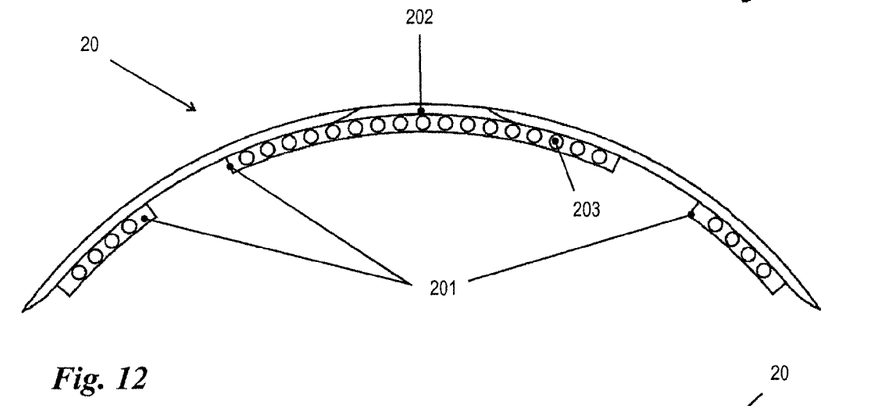
FIG. 12 a top view of the coil insert from FIG. 11.
Figure 13:
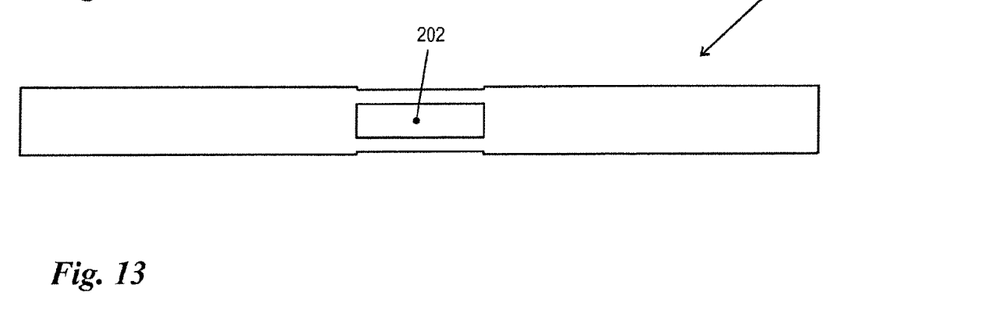
FIG. 13 a lateral view of the exterior side of the coil insert from FIG. 11.

FIGS. 11 to 13 show various views of a coil arrangement that is formed to correspond to the recess 165 in the outer side of the profile ring segments 161. In the embodiment shown, the coil arrangement 20 has coil carrier strips 201 on its axial edges which, when the stirrer arrangement 14 is in the assembled state, abut the axial mounting surfaces 167 of the profile ring segment 161. The coil carrier strips 201 are interrupted in certain areas to allow room for the axial bearings 164. In the area of the radial bearings 163, the coil inserts 20 have apertures 202 that provide the space necessary to accommodate the bearing elements.

Figure 16:
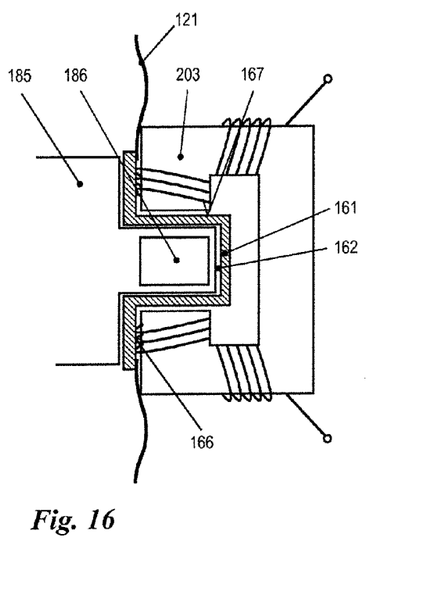
FIG. 16 a schematic view of an alternative coil/magnet configuration.

The actual coils 203 are only indicated schematically in the figures. Their exact design, orientation and electrical contacting are not shown, however can be realized in detail by one skilled in the art, taking into account the requirements of the individual case. FIGS. 15 and 16 show a highly schematized view of two possible designs for a coil. Of course, one skilled in the art will have to suitably coordinate the specific arrangement of the permanent magnets 186 in relation to the specific structure of the coils 203. One skilled in the art can also design the coordinated controlling of the coils or coil groups in the manner of a circularly curved linear motor, taking into account known electrical engineering aspects. Purely as an example, the standard orientations of the permanent magnets 186 in radial magnetization, axial magnetization and arrangement in a Halbach array are mentioned, each of which requires corresponding coil arrangements and controls.

Of course, the embodiments discussed in the specific description and shown in the figures are merely illustrative exemplary embodiments of the present invention. In the light of the present disclosure one skilled in the art has a broad spectrum of optional variations available.

LIST OF REFERENCE NUMBERS 10 bioreactor
12 reactor bag
121 bag wall
14 stirrer arrangement
16 profile ring
161 profile ring segment
162 guide groove
163 radial bearing
164 axial bearing
165 recess
166 radial mounting area
167 axial mounting area
18 rotor/stirrer
181 central body
182 impeller 183 cage
184 spoke
185 rim ring
186 permanent magnet
20 coil arrangement
201 coil carrier strip
202 aperture
203 coil

The invention claimed is:

1. A bioreactor, comprising
a reactor bag (12) having a predominantly flexible bag wall (121) with a rigidly formed bearing area in a segment of a height of the reactor bag (12),
a shaftless stirrer that is part of a rotor (18) that spans a cross-section of the bag (12), parts of the rotor (18) are permanently magnetic, the rotor (18) being housed in the bearing area inside of the bag,
a coil arrangement (20) positioned outside the reactor bag (12) and being operative to produce a rotating magnetic field that interacts with the permanent-magnetic parts of the rotor (18) to exert a torque on the rotor (18), and
a rigid profile ring (16) made of a non-magnetic material and having a guide rail (162/185), on which the rotor (18) is rotatably engaged, the profile ring (16) being arranged in the segment of the height of the reactor bag (12) along which the bearing area extends,
a magnetic field of the coil arrangement (20) interacting with at least one of the permanent magnet (186) parts arranged in a radially outer area of the rotor (18).

2. The bioreactor of claim 1, wherein
the profile ring (16) penetrates the flexible bag wall (121) and is bonded to the flexible bag wall (121).

3. The bioreactor of claim 1,
wherein
the profile ring (16) has a guide groove (162) running around the profile ring (16), the guide groove (162) being open towards the interior of the bag, into which guide groove (162) at least one guide shoe (185) arranged on a radially outer part of the rotor (18) is introduced axially and radially.

4. The bioreactor of claim 3,
wherein
at no fewer than three positions on a circumference of the profile ring (16), radially oriented roller bearings (163) and/or axially oriented, opposed pairs of roller bearings (164) project with spring action into the guide groove (162).

5. The bioreactor of claim 3,
wherein
at no fewer than three positions on a circumference of the profile ring, radially oriented slide bearing springs and/or axially oriented, opposed pairs of slide bearing springs project into the guide groove.

6. The bioreactor of claim 3,
wherein
on an outer side of the profile ring (16), the guide groove (162) forms a projection with at least one axial mounting surface (167) on which an electric coil arrangement (20) designed as a separate unit or unit group is arranged, the coil arrangement (20) being capable of generating the magnetic field.

7. The bioreactor of claim 6,
wherein
the guide groove (162) on the outer side of the profile ring (16) is surrounded on three sides, by form-fitting connection, by an electric coil arrangement (20) designed as a separate unit or unit group, the coil arrangement (20) being capable of generating the magnetic field.

8. The bioreactor of claim 1,
wherein
the rotor (18) has a central body (181) and at least three spokes (184) extending radially from the central body (181).

9. The bioreactor of claim 8,
wherein
the spokes (184) of the rotor (18) are connected to one another by a ring-shaped rim (185).

10. The bioreactor of claim 9,
wherein
the rim (185) has a plurality of permanent magnets (186) distributed around its circumference.

11. A reactor bag for a bioreactor (10), comprising: a predominantly flexible bag wall (121) with a rigid bearing area in a segment of a height of the reactor bag (12), and
a rigid profile ring (16) made of a non-magnetic material arranged in the bearing area in the segment of the height of the reactor bag (12) along which the bearing area extends, the profile ring (16) defining a guide rail (162/185).

12. The reactor bag of claim 11,
wherein
the profile ring (16) penetrates the flexible bag wall (121) and is bonded to the flexible bag wall (121).

13. The reactor bag of claim 11, further comprising:
a stirrer arranged in the interior of the bag and defining a shaftless rotor (18) spanning a cross-section of the bag and housed rotatably in an axial and radial manner on the profile ring (16) by means of the guide rail (162/185).

14. A stirrer to circulate the contents of a bioreactor (10) comprising:
a plurality of paddle-shaped circulation elements (182), a holder (183) at least partly surrounding the circulation elements (182) and fastened to the circulation elements (182),
at least three spokes (184) extending radially out from the holder (183), and
at least one rim ring (185) engaged with radially outer ends of the spokes (184), the at least one rim ring (185) having at least one permanent magnet (186) arranged in the at least one rim ring (185) and configured for engagement with an outer guide rail (162).

15. The stirrer of claim 14,
wherein
the spokes (184) of the rotor (18) are connected to one another by the rim ring (185), the at least one permanent magnet (186) defining a plurality of permanent magnets (186) distributed around the rim ring (185).

* * * * *